United States Patent [19]

Beran

[11] Patent Number: 4,723,543
[45] Date of Patent: Feb. 9, 1988

[54] ENDOTRACHEAL TUBE CONNECTOR

[76] Inventor: Anthony V. Beran, 1472 La Loma, Santa Ana, Calif. 92705

[21] Appl. No.: 801,929

[22] Filed: Nov. 26, 1985

Related U.S. Application Data

[63] Continuation-in-part of Ser. No. 460,587, Jan. 24, 1983, abandoned.

[51] Int. Cl.[4] .................................. A61B 5/08
[52] U.S. Cl. ............................ 128/207.14; 128/716; 128/719; 128/725
[58] Field of Search .............. 73/716, 720, 728, 726, 73/861.52, 861.55, 861.61, 861.64, 861.63, 198, 199, 201, 861.58, 861.65, 861.66; 128/207.16, 716, 719, 720, 725, 205.23, 912, 205.24, DIG. 26, 207.14, 207.15; D24/53; 285/172, DIG. 25

[56] References Cited

U.S. PATENT DOCUMENTS

| | | | |
|---|---|---|---|
| D. 245,921 | 9/1977 | Beran | D24/99 |
| 3,626,755 | 12/1971 | Rudolph | 73/205 L |
| 3,718,135 | 2/1973 | Diamond et al. | 128/719 |
| 3,960,142 | 6/1976 | Elliott et al. | 128/719 |
| 4,083,245 | 4/1978 | Osborn | 73/207 |
| 4,114,626 | 9/1978 | Beran | 128/DIG. 26 |
| 4,343,194 | 8/1982 | Pehart et al. | 73/861.65 |
| 4,346,584 | 8/1982 | Boehringer | 73/23 |
| 4,360,024 | 11/1982 | Wallace | 601/256 |
| 4,363,239 | 12/1982 | William | 73/204 |
| 4,368,740 | 1/1983 | Birder | 128/718 |
| 4,403,514 | 9/1983 | Osborn | 73/861.52 |
| 4,413,632 | 11/1983 | Schlossinger et al. | 128/716 |
| 4,440,177 | 4/1984 | Anderson et al. | 128/719 |
| 4,558,708 | 12/1985 | Labuda et al. | 128/719 |
| 4,558,709 | 12/1985 | Aida et al. | 128/719 |
| 4,566,480 | 1/1986 | Parham | 128/205.24 |

FOREIGN PATENT DOCUMENTS

| | | | |
|---|---|---|---|
| 23063 | 4/1962 | German Democratic Rep. | 128/207.16 |
| 1457411 | 12/1976 | United Kingdom | 604/256 |

OTHER PUBLICATIONS

"Pneumotachograph: A New, Low-Dead-Space, Humidity-Independent Device", Saklad et al., Anesthesiology, v 51, No. 2, Aug. 1979, 149-153.

*Primary Examiner*—Edward M. Coven
*Attorney, Agent, or Firm*—Price, Gess & Ubell

[57] ABSTRACT

A connector for a respirator apparatus which is adapted to be inserted into the open stem of a respiratory Y-tube and connected to an endotracheal tube is provided. In one embodiment the connector is adapted to be used as a pressure measuring or gas sampling device and in another embodiment as a pneumotach for measuring the respiratory flow rate of a patient. The dead space commonly encountered in prior art connectors is substantially reduced and the likelihood of disconnection is reduced or eliminated. The connector permits gas measurement adjacent the patient and at a cross sectional flow are that approximate the inner diameter of the endotracheal tube.

4 Claims, 21 Drawing Figures

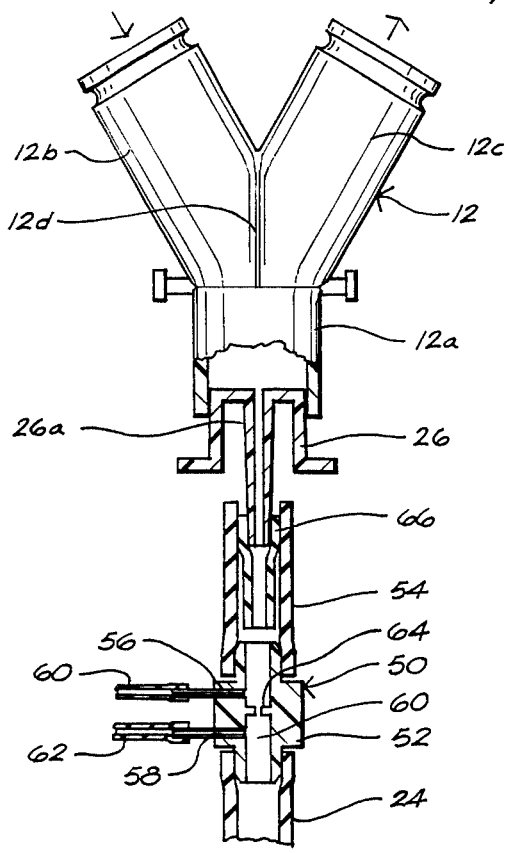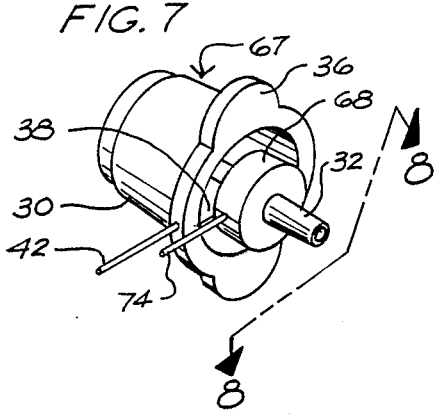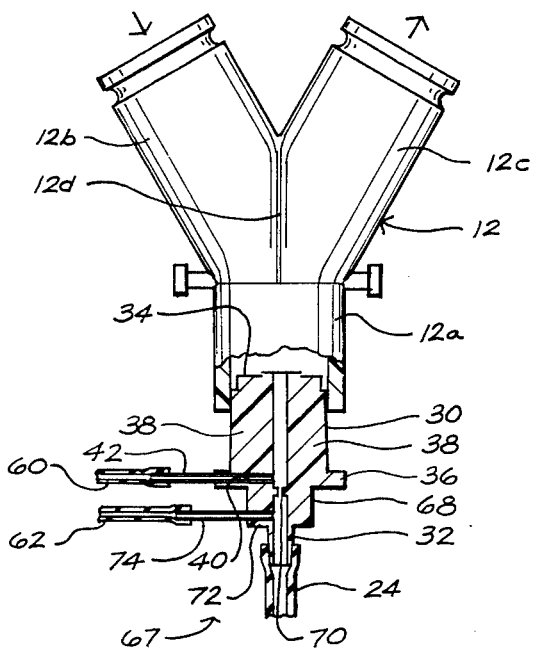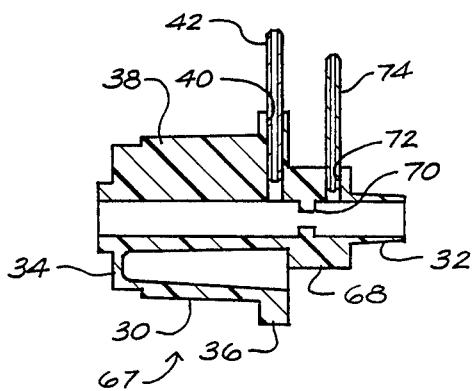

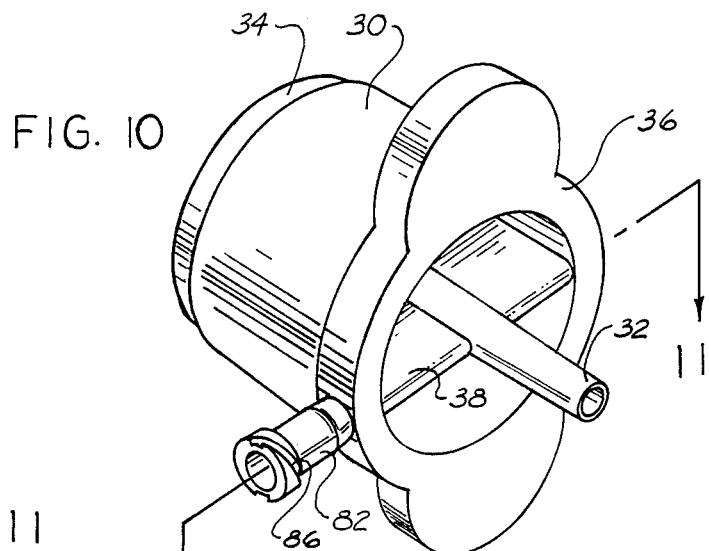
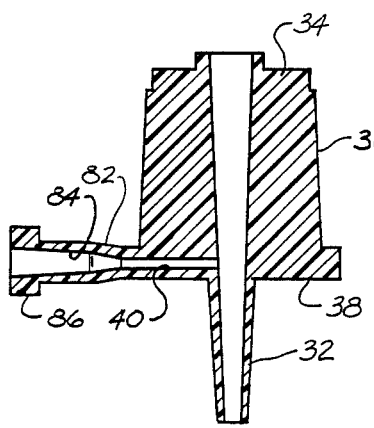
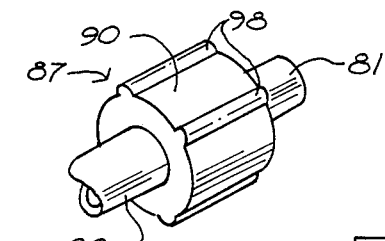
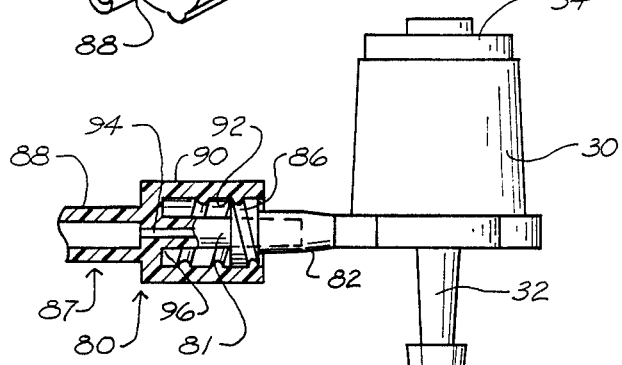
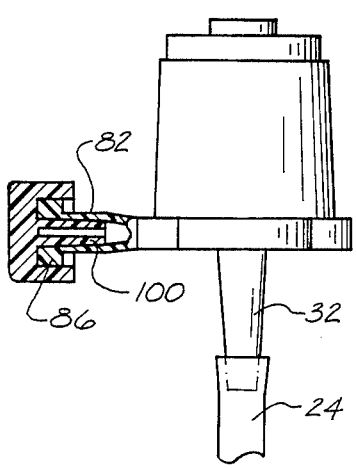
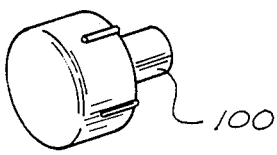

ENDOTRACHEAL TUBE CONNECTOR

RELATED APPLICATIONS

This application is a continuation in part of U.S. Ser. No. 460,587 filed on Jan. 24, 1983 for Connector for Respiratory Apparatus.

BACKGROUND OF THE INVENTION

FIELD OF THE INVENTION

This invention relates to an improved endotracheal tube connector that provides for sampling of respiratory gases, measuring of respiratory gas pressure, or respiratory flow of the patient.

BACKGROUND DISCUSSION

Respiratory apparatus is commonly employed to assist a patient in breathing. This apparatus, called a ventilator, is connected to two main lines which are independently connected into the two separate branched arms extending outwardly from the junction of a Y-tube. It is common practice to use an adaptor inserted into the open stem of the Y-tube to connect the Y-tube to an endotracheal tube extending from the trachea of a patient.

Different devices are sometimes employed when a patient is on a ventilator: One for measuring the respiratory pressure of exhaled gas, one for measuring composition of the exhaled gas, and one for measuring the respiratory flow of the patient. The patient's respiratory flow is the volume of gas the patient inhales and exhales in a given time period, and is usually expressed in liters per minute.

The respiratory flow is determined by measuring the change in pressure of this gas as it flows past a restriction in a tubular member. The tubular member is called a pneumotach. Such a pneumotach is described in the American Society of Anesthesiologists publication "Anesthesiology," Vol. 51, No. 2, pp. 149–153 entitled "Pneumotachography," by Saklad, Sullivan, Palitotta, and Lipsky. It consists of a main tube having a restriction therein and connecting tubes extending outwardly from this main tube on opposite sides of the restriction. There is a change in pressure as gases flow along the tube past the restriction, and this change is indicative of the respiratory flow of the patient.

In accordance with conventional practice, when any one of these devices are connected to the Y-tube, a substantial amount of dead space results. As explained in greater detail below, this dead space is highly undesirable and not only interferes with obtaining an accurate sampling of gases, but can present a health hazard to very small patients such as newborn babies. Moreover, the way these devices are connected is unsatisfactory because there is a high probability that they will become accidently disconnected.

SUMMARY OF THE INVENTION

The present invention is an endotracheal tube connector which connects the ventilator Y-tube and the endotracheal tube, and in one embodiment it serves as either a pressure measuring device or gas sampling device, and in a second embodiment serves as a pneumotach.

One embodiment of the connector of this invention includes a generally hollow cup member having a wall closing one end and an open mouth opposite the wall. The cup member is adapted to fit snug within the open stem of the Y-tube, with the closed end of the cup inserted into the stem. There is a flange element running about the edge of the open end of the cup member and integral therewith. A tubular conduit extends along the axis of the cup member and protrudes substantially from the open end. It also passes through the closed end and extends slightly beyond the wall closing off this end. In the preferred embodiment the internal cross-sectional area of the tubular conduit is about equal along its entire length and is about equal to the internal cross-sectional area of the endotracheal tube to which it is connected.

A pair of support members on the interior of the cup and on opposite sides of the tubular conduit are integral with the wall of the tubular conduit and the internal wall of the cup member. Preferably the support members are directly opposed to each other on opposite sides of the tubular conduit, and they preferably extend from the open end of the cup member up to the wall closing off the closed end of the cup member. These support members provide support for the tubular conduit and one of them has a passageway therein extending along its internal structure. This passageway extends from an opening in the flange along the inside of the support member to an opening in the tubular conduit. This passageway provides a narrow channel through which gases flowing through the conduit may be withdrawn. Tube means at the opening in the flange are provided so that the passageway may be placed in communication with tubing leading to either a gas analyzer or an instrument for measuring gas pressure.

In accordance with one feature of this invention, the tubular conduit extending from the open end of the cup is modified so that the connector can serve as a pneumotach. This modification consists of providing an enlarged body member integral with an intermediate portion of the tubular conduit protruding from the open end of the cup. There is a passageway extending from an opening in the body member through this structure to an opening in the tubular conduit. A restrictor piece is disposed in the tubular conduit between the first and the second openings in this tubular conduit. This restrictor piece has an orifice which has a cross-sectional area substantially less than the cross-sectional area of the tubular conduit. In the preferred embodiment the orifice area will be approximately 20% less than the area of the tubular conduit. In accordance with this embodiment of the invention, there are two tubes extending outwardly from the connector which are, respectively, in communication with the two separate passageways that terminate on opposite sides of the restrictor piece. These tubes are connected through flexible tubing to the appropriate monitoring apparatus which is adopted to measure the pressure differential across the restrictor piece to provide a measurement of the respiratory flow. The passageway can be located in a flange adjacent a closed end with the tubular conduit extending exterior of the closed end in another embodiment of the invention.

The connector of this invention has several advantages. It may be made entirely out of plastic as an integral structure. Thus it is easy to manufacture. If desired, however, the tubes in the passageways may be made of metal and inserted into the passageways. Because the connector also serves as an adaptor which is inserted directly into the stem of the Y-tube, there are fewer connection junctions, therefore reducing the possibility of leakage and disconnect since the number of such junctions has been reduced. An advantage of one form of this invention is that dead space previously occurring using conventional connectors can be substantially reduced. This reduces the danger to small patients, and improves the accuracy of gas sampling.

BRIEF DESCRIPTION OF THE DRAWINGS

FIG. 6 is a side elevational view, with sections broken away, showing the prior art way of connecting a pneumotach to a respiratory Y-tube.

FIG. 7 is a perspective view of a second embodiment of this invention designed to serve as a pneumotach.

FIG. 8 s a cross-sectional view taken along line 8—8 of FIG. 7.

FIG. 9 is a side elevational view, with sections broken away, showing the connector shown in FIG. 7 inserted into the Y-tube of respiratory apparatus.

FIG. 10 is a perspective view of a third embodiment of this invention, which is a modification of the device shown in FIG. 2, wherein the sampling tube is designed to be securely attached to the pressure measuring or gas analyzing instruments.

FIG. 11 is a cross-sectional view taken along line 11—11 of FIG. 10.

FIG. 12 is a perspective view of the end of the line from an instrument connected to the sampling tube extending from the device shown in FIG. 10.

FIG. 13 is a side elevational view, partially in cross-section, showing the line from an instrument connected to the device shown in FIG. 10.

FIG. 14 is a side elevational view of the device shown in FIG. 10 with the sampling tube sealed off by a cap inserted into it.

FIG. 15 is a perspective view of the cap shown in FIG. 14.

DETAILED DESCRIPTION OF THE DRAWING

Figure 1:
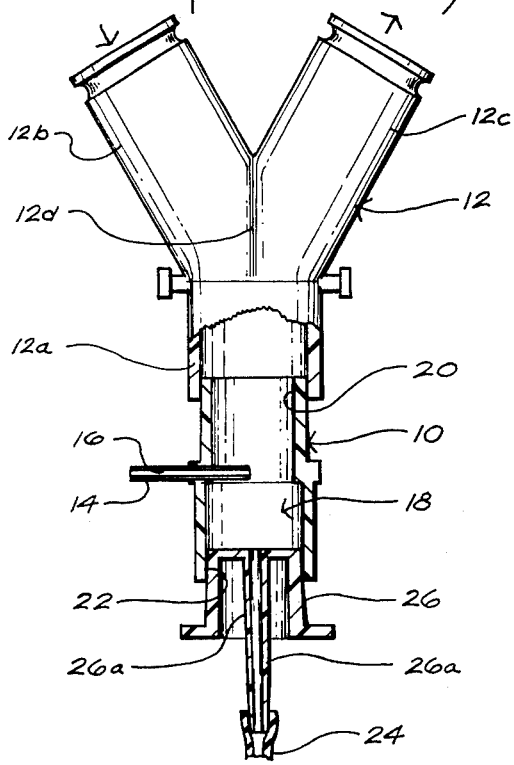
FIG. 1 is a side elevational view, with sections broken away, showing the prior art way of connecting a pressure measuring device to a Y-tube used with a ventilator.

As shown in FIG. 1, a conventional gas samping device 10 is inserted into the open end of the stem 12a of a respiratory Y-tube 12. The two branched arms 12b and 12c of the Y-tube are connected, respectively, to the inhalation and exhalation tubes (not shown) of a ventilator (not shown), and merge at the junction 12d to form the stem 12a. The gas sampling device 10 includes a tube 14 which leads through a passageway 16 into a chamber 18 within the device. This chamber 18 has a relatively large volume and has open ends 20 and 22.

When the patient inhales, air is pushed through the branched arm 12b and stem 12a, through the sampling device 10, and then into the patient's lungs through an endotracheal tube 24 which is connected at its remote end to an adaptor 26 which fits into the open end 22 of the gas sampling device. The adaptor 26 is of the type shown in U.S. Pat. No. 4,114,626.

When the patient exhales, a valve (not shown) in the ventilator opens the one side of the ventilator and closes off the other, so that the exhaled gases are exhausted through the branched arm 12c and not the other arm 12b. These exhaled gases flow through the endotracheal tube 24 along a tubular conduit 26a in the adaptor into the chamber 18 and then out the opening 20 through the branched arm 12c. A small portion of both inhaled and exhaled gases is pulled by suction through the tube 14 into a gas analyzer (not shown).

The chamber 18 provides a substantial volume of dead space. When gases exit the patient they are mixed with the gas in this dead space. This dilutes the gases being expelled by the patient and this mixture is then withdrawn from the chamber 18 through the tube 12c and forwarded to the gas analyzer. This dilution or contamination results in an inaccurate sampling of the gas being exhausted from the patient.

Another disadvantage of the dead space is that, for patients having a low tidal volume, the dead space substantially impairs the patient's ability to remove carbon dioxide ($CO_2$). Tidal volume is the difference between the lung volume at the end of exhalation and the lung volume at the end of inhalation. Assume that the ventilator is connected to a newborn body who has a tidal volume of only 5 cubic centimeters and that the volume of the chamber 18, the dead space, is 2.5 cubic centimeters. That is, the dead space is 50% of the tidal volume. As carbon dioxide is expelled from the baby, this dead space is filled with this gas. Since the baby's lungs ordinarily contain some carbon dioxide, the carbon dioxide from the dead space added to the carbon dioxide in the lungs, impairs the ability of the lungs to cleanse the blood of carbon dioxide. In very small patients having low tidal volume this is a very dangerous condition.

Figure 5:
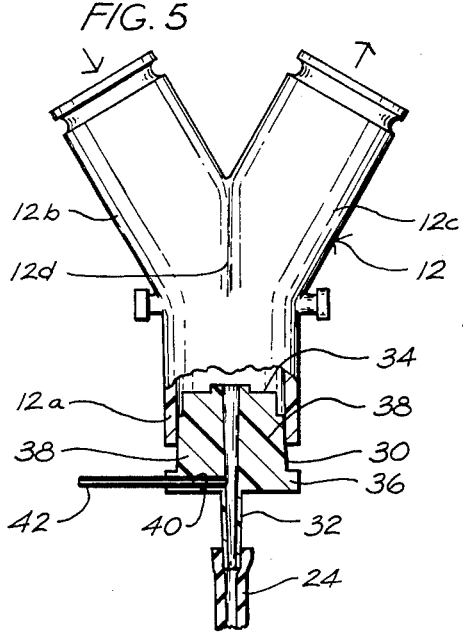
FIG. 5 is a side elevational view, with sections broken away, showing the connector shown in FIG. 2 inserted into the Y-tube of respiratory apparatus.
Figure 2:
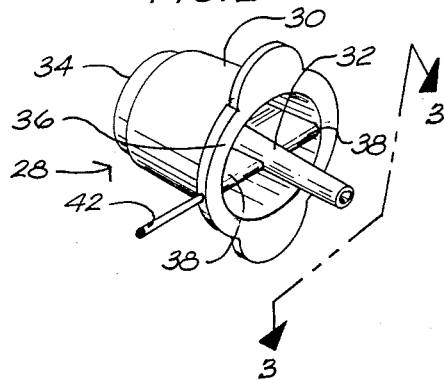
FIG. 2 is a perspective view of one embodiment of this invention used to measure the pressure or sample respiratory gases for analysis.
Figure 3:
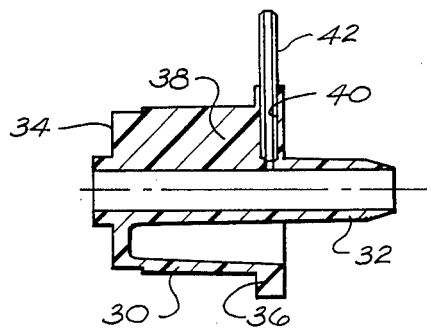
FIG. 3 is a cross-sectional view taken along line 3—3 of FIG. 2.
Figure 4:
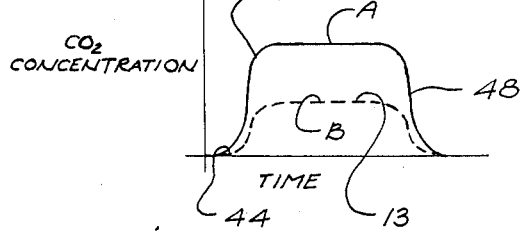
FIG. 4 is a graph illustrating the improved gas sampling obtained using the present invention.

The present invention substantially reduces the dead space as can be appreciated upon considering FIGS. 2, 3, 4, and particularly FIG. 5. As shown in these Figures, the connector 28 of the present invention, which is designed to be used as a pressure measuring device, is inserted directly into the stem 12a of this Y-tube. Consequently, a large portion of the dead space is eliminated.

This connector 28 includes a cup member 30 having an elongated tubular conduit 32 running along the longitudinal axis of the cup member. The cup member has a wall 34 which closes off one end of the member, and the conduit 32 has a small portion extending through this wall. The other end of the cup member is open and a relatively large portion of the conduit 32 extends beyond this end. Two support members 38 on opposite sides of the conduit hold the conduit in a fixed position with respect to the cup member. These support members are inside of the cup member and are integral with both the wall of the tubular conduit and the inside of the wall of the cup member. A flange 36 is integral with the edge of the side wall of the cup member extends around the open mouth. There is a passageway 40 extending from an opening in the flange along the inside of one of the support member 38 to an opening terminating in the wall of the tubular conduit 32. Inserted into this passageway is a metal tube 42. The metal tube 42 could be eliminated as a separate piece by forming a similar tube from plastic during molding or by forming a Luer lock fitting as illustrated in FIGS. 10 through 15.

The graph of FIG. 4 illustrates the improved gas sampling obtained using the connector 28. As shown by this graph, $CO_2$ concentration in exhaled gases are measured over time, comparing the $CO_2$ concentration derived using the connector 28 with that derived using the prior art device 10. When the patient inhales, gas flows through the branched arm 12b and the conduit 32 into the endotracheal tube 24. At the same time some of the inhaled gas is drawn by suction through the passageway 40 and tube 42 into the gas analyzer. There is essentially no $CO_2$ in the sampled gas during inhalation, and this condition is illustrated by the section 44 of curves A and B. When the patient exhales, gases flow through the endotracheal tube 24, through the tubular conduit 32 out the arm 12c of the Y-tube. At the same time some gas will flow through the passageway 40 and out the tube 42 into the analyzer. At this time, the gas flowing into the analyzer has in it a high level of carbon dioxide. This condition is illustrated by the increase in $CO_2$ level indicated by the section 46 of the curve A. When the patient again inhales, the level of $CO_2$ will drop. This is illustrated by the section 48 of curve A. As shown in curve B, the same generally shaped curve will be provided using the prior art device 10. The level of $CO_2$ concentration in the exhaled gas will, however, be substantially less than that sampled by the connector 28, because of the dilution of exhaled gas with gas in the dead space. Thus the present invention provides a more sensitive and accurate measurement of $CO_2$ in exhaled gases.

As shown in FIG. 6, a conventional pneumotach 50 is connected via the adaptor 26 to the respirator Y-tube 12. This pneumotach 50 includes a body section 52 having two open ends which are, respectively, connected to the endotracheal tube 24 and to an intermediate tube 54. The intermediate tube 54 is connected to the adapter 26 which is inserted into the stem 12a of the Y-tube. There are two passageways 56 and 58 extending outwardly from a central passageway 60 of the pneumotach. These passageways 56 and 58 are connected, respectively, by tubes 60 and 62 to a differential pressure transducer (not shown). As gases flow past a restrictor 64 in the central passageway 60, there is a drop in pressure. This drop or differential in pressure is measured by a transducer and appropriate electronics (not shown) which then converts it into a reading corresponding to the patient's respiratory flow.

Sometimes it is necessary to use a tube 66 of smaller diameter which will fit on the conduit 26a of the adaptor 26, and then the larger diameter tube 54 connected to the outlet of the pneumotach is fitted over this smaller tube. Also, tape is sometimes used to tape the pneumotach to the endotracheal tube. This way of attaching the pneumotach 50 to the respirator Y-tube 12 is not only burdensome and clumsy, but there is substantial dead space within the various tubes which, as discussed above, presents a danger to small patients. Moreover, the multiple connection junctions provide several routes for gas leakage or disconnect.

As illustrated in FIGS. 7, 8 and 9, the second embodiment of this invention provides a connector 67 which is adapted to be used as a pneumotach and which provides a simplified way of attaching the endotracheal tube 24 to the respirator Y-tube 12, and at the same time minimizes the dead space. This connector also includes the cup member 30 having the tubular conduit 32 running along the longitudinal axis of the cup member, the pair of support members 38 on opposite sides of the tubular conduit, and the passageway 40 leading into the conduit, including the outwardly projecting tube 42. These elements are essentially the same as comparable elements making up the connector 28 shown in FIGS. 2 and 3, with the exception that the intermediate portion of the tubular conduit 32 extending from the open end of the cup member includes an enlarged body member 68. This body member has a restrictor 70 and a passageway 72 leading between an opening in the surface of the body member to an opening in the conduit 32. A metal tube 74 extends into this passageway. This arrangement thus provides a pneumotach where the restrictor is between the ends of the two passageways 40 and 72.

As shown in FIG. 9, the connector 68 is inserted into the open end of the stem 12a and the tubular conduit 32 is inserted into the open end of the endotracheal tube 24. The tubes 42 and 74 are then connected by the tubing 60 and 62 to the differential pressure transducer (not shown). In operation, as gases flow through the tubular conduit 32 past the restrictor 70, there is a pressure differential across the restrictor which is measured by the transducer connected to the tubes 60 and 62. The differential pressure transducer and associated electronics converts this into a numerical display of the respirator flow of the patient.

The embodiment shown in FIGS. 10 through 15 is similar to the embodiment shown in FIGS. 2 through 5, except the tube 42 has been eliminated. Instead of this tube 45 a Luer lock fitting 80 (FIG. 13) is employed which securely, but removably, attaches the connector to an instrument. This fitting includes a male member 81 and a female member 82 which are integral with the cub member 32. The female member 82 has an open-ended cavity 84 aligned with and in communication with the passageway 40. The cavity 84 is tapered so that the one open end adjacent the passageway 40 is about equal to the diameter of the passageway and the opposed open end has a substantially larger diameter. The connecting end of the female member 82 has a threaded section 86.

The male member 81 is part of an assembly 87 which is integral with, or connected to, the end of tubing 88 extending from the gas analyzer (not shown). The assembly 87 includes a cap 90 having an internal threaded section 92. The tubing 88 terminates in a passageway 94 extending longitudinally through the male member which has its one end integral with the internal back wall 96 of the cap 90. The external walls of the cap have ribs 98 integral therewith for assisting in screwing the cap on the female member 82, with the male member inserted into the female member. Tightening the cap creates a seal between the male and female members and securely attaches the connector to the tubing 88. Thus, there is no leakage of gas at this point of connection, and the possibility of accidental disconnection is eliminated. Nevertheless, the device may be readily disconnected from the gas analyzer when desired by simply unscrewing the cap.

In some instances it is not necessary to sample gas or measure gas pressure. In this case the male member 81 is removed from the female member. A plug 100 is then inserted into the female member as shown in FIG. 14. This plug closes off the passageway 40 and prevents gas leakage from the passageway.

Figure 16:
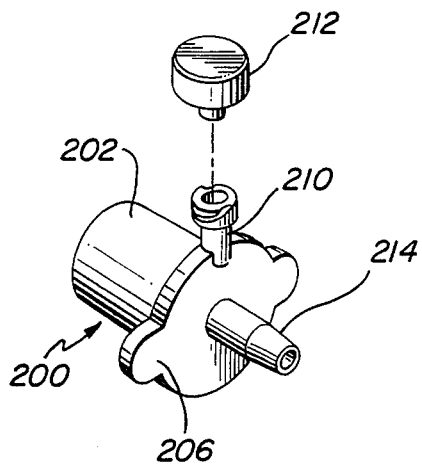
FIG. 16 is a side elevational view, of another embodiment of the invention.
Figure 17:
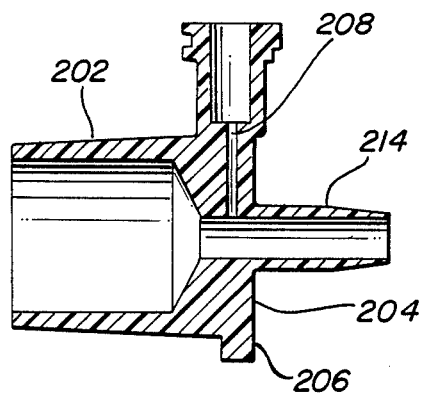
FIG. 17 is a cross-sectional view of the device shown in FIG. 16.
Figure 18:
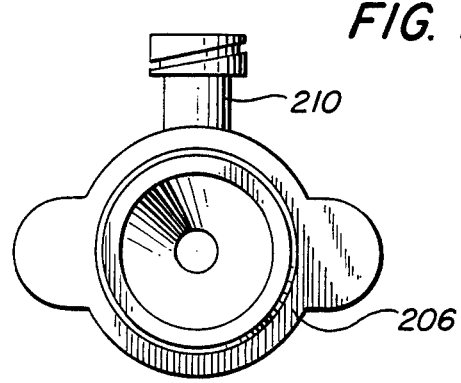
FIG. 18 is a rear elevational view of the device shown in FIG. 17.

Another embodiment of the invention is disclosed in FIG. 16 wherein the connector 200 has a cylindrical connector collar 202 with an outside diameter sized to provide a frictional fit with the inside diameter stem of the Y-tube. The end wall 204 closes the collar 202. A flange member 206 extends radially outward from the end wall 204.

A passageway 208 extends from the interior of a tubular conduit 208, through the end wall 204 and the flange 206 to a Luer fitting stem 210 that can be closed with a cap 212.

Finally, the tubular conduit 214 has an exterior outer diameter slightly greater than the inner diameter of an endotracheal tube and an inner diameter approximately the size of the inner diameter of an endotracheal tube. The endotracheal tube (not shown) can be friction fitted on the tubular conduit 214.

Thus in those instances where dead space is not as relevant an issue, e.g. adult patients, the connector 200 can be utilized to not only interconnect the Y-stem and the endotracheal tube but also to serve a dual function of measuring the gas.

The present invention provides with one structure a connected betwen a conventional Y-stem and an endotracheal tube that eliminates the necessary connections of supplemental parts such as shown in FIGS. 1 and 6 to take appropriate measurements of the gases flowing through the tubular conduit. Thus, one connector part replaces numerous elements that were required in the prior art. Additionally, this one part permits a testing adjacent the patient at a cross-sectional flow area that approximates that of the endotracheal tube.

It is a common practice to use an adaptor (15 mm endotracheal tube connector) inserted into the open stem of the Y-piece to connect the Y-piece to an endotracheal tube extending from the trachea of a patient.

Endotracheal tubes with associated 15 mm connectors are available in at least 15 different sizes from 2.5 to 10 mm I.D. to cover a variety of anatomical and physiological requirements found in newborn, pediatric, and adult patients.

Several physiological variables have to be measured in order to adjust the ventilator or anesthesia machine for safe and efficient ventilatory support of the patient. Some of the variables measured are proximal airway pressure, respiratory flow, and inspiratory and expiratory gas composition. Measurements of these variables under presently available clinical conditions are unreliable, fraught with complications and require improvements.

Measurements of airway pressure is important because lungs ventilated with insufficient pressure will produce insufficient $O_2$ and $CO_2$ exchange. On the other hand, lungs ventilated with excessive pressures can produce decreased pulmonary venous return which lowers cardiac output and/or causes a pneumothorx.

The issue of where the airway pressure should be measured is important. In a ventilator conduit comprises of many different inside diameters and materials of different compliances, the dynamic pressures change at different points along the conduit. These changes in pressure depend on many different variables such as compliance of the conduit segment, radius of conduit at the pressure measurement site, frequency of the dynamic pressure changes, leaks, constrictions, etc.

The airway pressure which results in $O_2$ and $CO_2$ exchange and affects cardiac output and/or causes a pneumothorax is the intra-alveolar pressure. Under routine clinical conditions, direct measurement of dynamic intra-alveolar pressure is not feasible. Therefore, measurement of airway pressure which most closely approximates intra-alveolar pressure at a clinically practical measurement site is the compromise which must be made.

The pressure drops along the ventilator conduit are most profoundly influenced by the radius of the inside of the conduit and lesser influenced by its length. Thus, the second best location to monitor airway pressure, therefore, is in the patient's upper airways or in the trachea. However, this location also presents significant practical difficulties in a clinical setting. The present inventor has concluded that the best compromise location is in the endotracheal connector where the I.D. is equivalent to the I.D. of the endotracheal tube.

Thus our inventive connector permits clinically practical airway pressure measurements at a location in the connector where the I.D. is equivalent to the I.D. of the endotracheal tube thus reflecting with greater accuracy the pressures in the patient's airway under all physical and clinical conditions.

Measurement of respiratory flow is equally important because a sufficient volume of air has to be delivered for optimal gas exchange. The patient's respiratory flow is the rate of change in the volume of gas which the patient inhales and exhales and is usually expressed in liters per minute. The respiratory flow is determined by measuring the change in pressure of this gas as it flows past a restriction in a tubular member such as a pneumotach. Such a pneumotach is described in the American Society of Anesthesiologists publication "Anesthesiology," Vol. 51, No. 2, pp. 149–153 entitled "Pneumotachography," by Saklad, Sullivan, Palitotta, and Lipsky. It consists of a main tube having a restriction therein and connecting tubes extending outwardly from this main tube on opposite sides of the restriction. There is a change in pressure as gases flow along the tube past the restriction, and this change is quantitatively related to the respiratory flow of the patient.

A problem which occurs in the practical clinical application of a pneumotach is that the quantitative relationship between the pressure drop and flow for any single sized device becomes nonlinear over some part of the flow ranges found in clinical situations. The solution to this problem implemented in our connector is to have the pneumotach as part of the connector sized to a matching size endotracheal tube. The pneumotach is tailored to exhibit a linear sensitivity to flow over the flow range present in patients using that particular sized tube.

Measurement of inspiratory and expiratory gases also depends on which point of the ventilator s circuit the gases are sampled from. Gases flowing in a large conduit exhibit concentration profiles within the conduit similar to a pressure profile. The gas concentration along the wall of the conduit approximates the mean or average concentrations. The dynamically changing the concentrations are more evident near the center of the conduit. As the conduit becomes larger in diameter, this phenomenon becomes more evident. By measuring gas concentration at the I.D. equivalent to the I.D. of the endotracheal tube, the gas flow in this location is probably turbulent and the concentration profile does not exist. The net result is more precise measurement of inspiratory and expiratory gas concentrations.

In addition, in accordance with conventional practice, when any one of these additional devices are connected to the Y-piece, a substantial amount of dead space results. This dead space is highly undesirable and not only interferes with obtaining an accurate sampling of gases, but can present a health hazard to very small patients such as newborn babies. Moreover, the way these devices are connected is unsatisfactory because of a probability that they will become accidentally disconnected.

Figure 21:
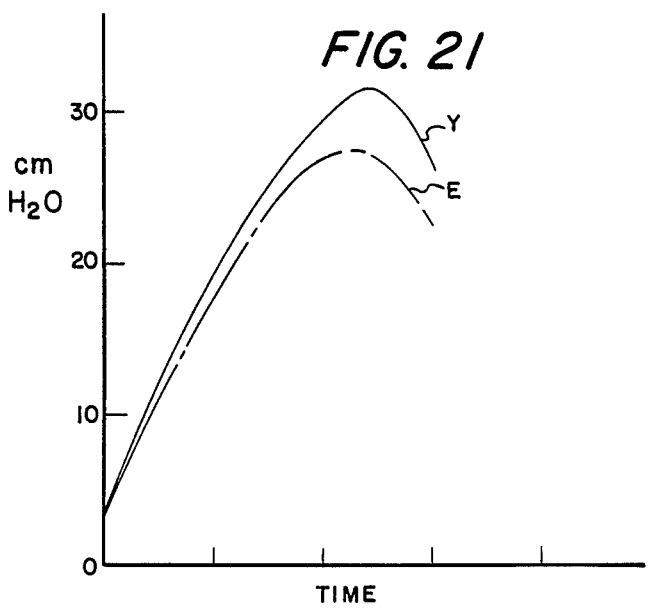
FIG. 21 is a graph of pressure measurements.

A pressure drop occurs in the ventilator circuit from the pressure source (ventilator) to the patient's airways. A substantial pressure drop occurs in the ventilator circuit where the I.D. of the circuit is reduced to the I.D. of the endotracheal tube. The connector of FIG. 1 will measure the pressure prior to this pressure drop. The connectors of the present invention will measure pressure after this drop because the pressure sampling port is located in a portion of the connector where the I.D. is equivalent to the I.D. of the endotracheal tube. This results in a more accurate measurement of pressure that actually is applied to the patient's airway thus permitting optimal ventilator adjustment. The difference in pressure measured depends on peak pressure and flow rate and can be as high as 10 cm of water, which is clinically significant see FIG. 21 wherein pressure measurements at the "Y" of the ventilator (Y curve) are compared with pressure measurements at the tubular conduit of the connector (E curve) of the present invention. The pressures were measured with a pressure transducer with a Bourns (T.M.) Ventilator connected to a 3 mm I.D. endotracheal tube and a Bourns (T.M. lung simulator. The ventilator system pressure was the same for both measurements.

Patients requiring intubation are intubated with different tube sizes based on their anatomical and phhsiological requirements. Each tube size has a matching connector. Flow requirement in small patients are smaller than in large patients, therefore a pneumatch used in large patients would have insufficient sensitivity to flow changes found in small patients. By providing a pneumatch in the form of a 15 mm connector which matches a specific tube size, optimal flow sensitivity can be achieved for the flow range found in a specific patient.

Figure 20:
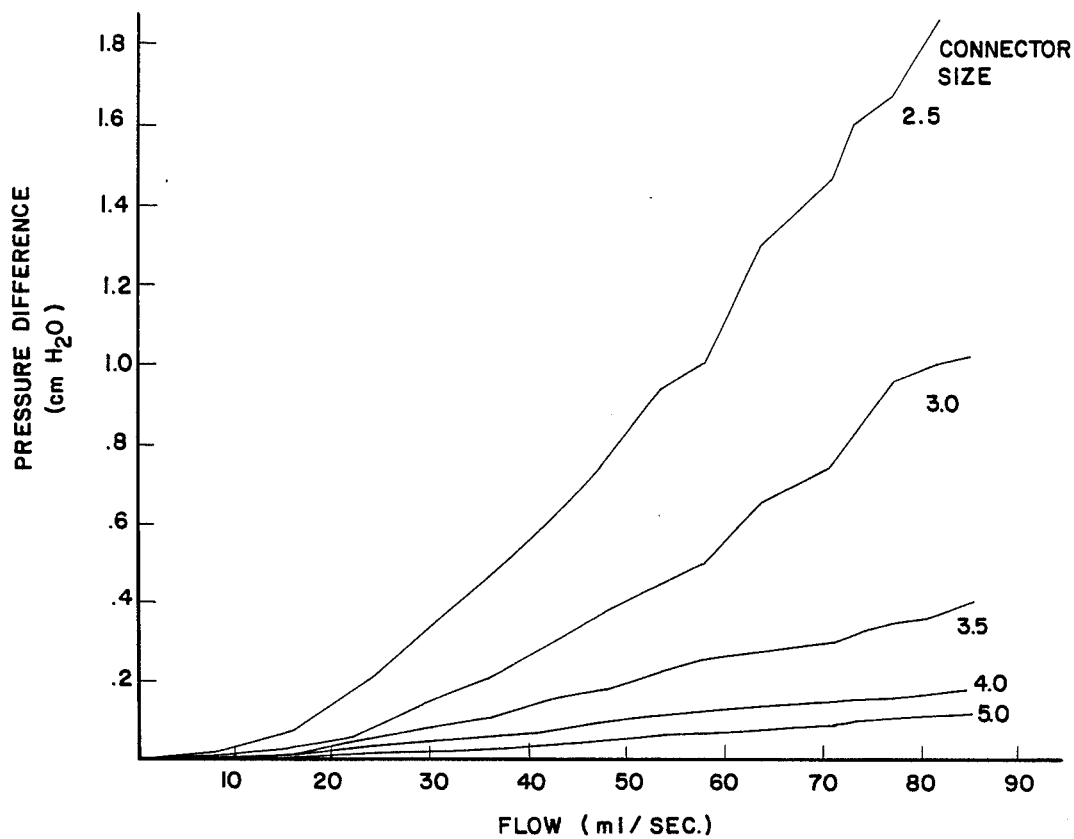
FIG. 20 is a graph of sensitivity curves of connector sizes and pressure vs. flow.

As the connector size decreases, the flow sensitivity increases, making a 2.5 mm connector more sensitive than a 5.0 mm connector, see the connector size versus pneumotach sensitivity curves of FIG. 20. This lends itself to a very suitable clinical application, because flows in patients using 2.5 mm connectors are small and greater sensitivity is required. By incorporating a pneumatch with a 15 mm connector in a size range from 2.5 to 10.0 mm I.D., a variable sensitivity approach with high resolution and linearity over the expected flow range within which each connector would be used, has been accomplished by the present invention.

Figure 19:
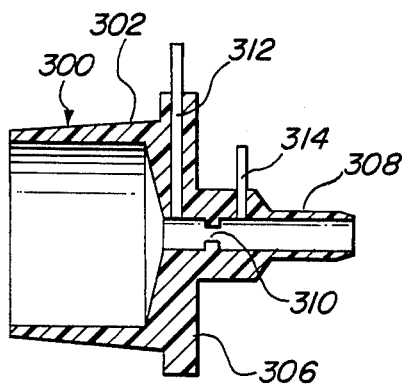
FIG. 19 is a cross-sectional view, of another embodiment of the invention designed to also serve as a pneumotach.

A final embodiment of the invention is disclosed in the cross-sectional view of FIG. 19 for use as a combined connector pneumotach 300. A cylindrical connector collar 302 with an outside diameter sized to provide a frictional fit with the inside diameter stem of a Y-tube is provided. The end wall 304 closes the collar 302. A flange member 306 extends radially outward from the end wall 304. A tubular conduit 308 is cantilevered from the end wall 304 and provides a restrictor 310 between one open end of the tubular conduit 308 and its other open end in communication with the connector collar. A first passageway 312 extends from one side of the restrictor 310 in the tubular conduit 308, through the end wall 304 and flange member 306 for connection to a flow measuring device. A second passageway 314 is on the other side of the restrictor 310 and likewise extends through the tubular conduit 318 for connection to a flow measuring device. Because the flows are measured at an I.D. similar to the I.D. of the endotracheal tube linearity in measurement can be achieved.

The above description presents the best modes contemplated of carrying out the present invention. This invention is, however, susceptible to modifications and alternate constructions from the embodiments shown in the drawings and described above. For example, the tubes 42 and 74 of the pneumotach shown in FIGS. 7, 8, and 9 could be replaced by Luer lock fittings of the type shown in FIGS. 10 through 15. Consequently, it is not the intention to limit this invention to the particular embodiments disclosed; but on the contrary, the invention is to cover all modifications and alternate constructions falling whin the spirit and scope of the invention as expressed in the appended claims.

I claim:

1. In a respiratory support system for a patient including a Y-tube with a stem connected to a ventilator and an endotracheal tube, the improvement comprising:

a connector for attaching the Y-tube stem to the endotracheal tube including a hollow cylindrical cup member with a closed axial end having an outer circumference adapted for sealing contact with the Y-tube stem; a flange element attached to the hollow cup member and extending outwardly and laterally away from the outer circumference of the cup member, the flange member including an opening on its peripheral surface; a tubular conduit, connected to the hollow cup member extending along the axis of the hollow cup member and protruding from the closed axial end of the hollow cup member, the tubular conduit having an inner diameter that approximates the inner diameter of the endotracheal tube and an outer diameter that is adapted for connection to the endotracheal tube, the tubular conduit having opposed open ends so that gases may flow between the Y-tube stem and the endotracheal tube, the tubular conduit has a port opening on its inner diameter positioned intermediate the open ends of the tubular conduit; a passageway extending from the peripheral flange member opening, through the flange element and cup member to terminate with the port opening in the tubular conduit to provide channel through which gases flowing through the tubular conduit may be withdrawn from the conduit, and means for connecting to the flange member peripheral opening to permit passage of the gases drawn from the tubular conduit.

2. The connector of claim 1 wherein the connector is molded from a plastic material to form an integrated unitary structure.

3. The connector of claim 2 wherein the means for connecting includes a Luer fitting extending from the flange element.

4. The connector of claim 2 wherein the hollow cup member axial end wall member has an opening aligned with the tubular conduit, the end wall member is concentric to the flange member and the passageway port opening is positioned adjacent one end of the tubular conduit adjacent the opening in the end wall member whereby measurement of the gas flow can more accurately approximate the flow range to the patient.

* * * * *